United States Patent
Kaess et al.

(10) Patent No.: US 8,465,202 B2
(45) Date of Patent: Jun. 18, 2013

(54) MICROSTRUCTURED SENSOR FOR THE DETECTION OF IR RADIATION

(75) Inventors: Udo Kaess, Stuttgart (DE); Christian Lemier, Reutlingen (DE); Markus Niemann, Beckingen (DE)

(73) Assignee: Robert Bosch GmbH, Stuttgart (DE)

( * ) Notice: Subject to any disclaimer, the term of this patent is extended or adjusted under 35 U.S.C. 154(b) by 261 days.

(21) Appl. No.: 12/924,584

(22) Filed: Sep. 29, 2010

(65) Prior Publication Data
US 2011/0110394 A1    May 12, 2011

(30) Foreign Application Priority Data
Oct. 2, 2009    (DE) ................ 10 2009 045 302

(51) Int. Cl.
*G01J 5/12*     (2006.01)
*G01K 7/02*     (2006.01)
*G01J 3/00*     (2006.01)

(52) U.S. Cl.
USPC ............... 374/121; 374/179; 374/45; 374/17; 374/129; 356/451

(58) Field of Classification Search
USPC ............. 374/120, 121, 129, 163, 100, 179, 374/16–18, 28, 161; 250/338.1; 73/866.5, 73/19.01, 23.25, 23.37, 24.05, 25.01; 356/451
See application file for complete search history.

(56) References Cited

U.S. PATENT DOCUMENTS

| | | | | |
|---|---|---|---|---|
| 4,928,513 | A | * | 5/1990 | Sugihara et al. ............ 73/25.03 |
| 6,034,369 | A | * | 3/2000 | Oda .......................... 250/338.1 |
| 6,102,564 | A | * | 8/2000 | Egawa ......................... 374/129 |
| 6,203,194 | B1 | * | 3/2001 | Beerwerth et al. ........... 374/133 |
| 6,495,829 | B1 | * | 12/2002 | Oda ......................... 250/339.02 |
| 7,780,343 | B2 | * | 8/2010 | Chen et al. ..................... 374/45 |
| 8,215,831 | B2 | * | 7/2012 | Ernst et al. ..................... 374/121 |
| 2005/0161605 | A1 | * | 7/2005 | Yokura et al. ................ 250/343 |
| 2006/0169902 | A1 | * | 8/2006 | Watanabe ................. 250/338.1 |

FOREIGN PATENT DOCUMENTS

| | | | |
|---|---|---|---|
| DE | 10 2007 021 911 | | 11/2008 |
| EP | 1022551 A2 | * | 7/2000 |
| JP | 63233339 A | * | 9/1988 |
| JP | 04183270 A | * | 6/1992 |

* cited by examiner

*Primary Examiner* — Gail Verbitsky
(74) *Attorney, Agent, or Firm* — Kenyon & Kenyon LLP

(57) ABSTRACT

A microstructured sensor for detecting IR radiation includes: one measuring channel having a measuring diaphragm, on which a first sensitive detector surface is implemented for the absorption of a first IR radiation; and one reference channel having a reference diaphragm, on which a second sensitive detector surface is implemented for the absorption of a second IR radiation. A measuring structure, e.g., a thermopile measuring structure as a series circuit made of thermocouple pairs, is implemented between the measuring diaphragm and the reference diaphragm for measuring a temperature differential between the measuring diaphragm and the reference diaphragm. First and second thermal contacts lie alternately on the two diaphragms.

9 Claims, 2 Drawing Sheets

MICROSTRUCTURED SENSOR FOR THE DETECTION OF IR RADIATION

BACKGROUND OF THE INVENTION

1. Field of the Invention

The present invention relates to a microstructured sensor for the detection of IR radiation.

2. Description of Related Art

Microstructured multichannel infrared sensors are used in particular as spectroscopic or photometric gas sensors, in which a measuring channel detects the intensity of the incident IR radiation of the gas-specific measuring wavelength range and a reference channel detects the intensity of the incident. IR radiation of a reference wavelength range.

For this purpose, photometric gas sensors generally have an IR radiation source, an absorption section for receiving a gas mixture to be studied, and an infrared detector having bandpass filters for the wavelengths. In general, at least one absorption band of the gas to be detected is in the measuring wavelength range, such as a carbon oxide COx or nitrogen oxide NxO; no noticeable absorption preferably occurs due to a gas in the reference wavelength range. In addition to the use as spectroscopic gas sensors, microstructured infrared sensors may further also be used as thermoelements for temperature measurement.

Published German patent application document DE 10 2007 021 911 A1 discloses a gas sensor of this type, which is implemented in microstructured form on a sensor chip. For this purpose, a measuring diaphragm is implemented cantilevered over a cavity of the sensor chip in the measuring channel, which has an absorber layer for absorbing the incident IR radiation on its upper side, for example, and thus heats up as a function of the IR radiation. The reference channel is similarly constructed having a reference diaphragm over a cavity and in general largely symmetrically to the measuring channel, in order to allow identical measuring conditions for the reference measurement as much as possible.

A sensitive structure for the detection of the IR radiation or the heating caused by the IR radiation is implemented on each of the diaphragms, the sensitive structure being able to be implemented, for example, as a bolometric, a pyroelectric, or as a thermopile structure having a series circuit of multiple thermocouple pairs made of two thermopile legs each. In each channel, the thermopile legs are implemented from materials having different Seebeck coefficients and extend from the bulk material outside the diaphragm to the diaphragm, contacting with one another in hot contacts on or in the diaphragm and in cold contacts in the bulk area, so that hot and cold contacts are implemented alternately in the series circuit. The temperature of the diaphragm of each channel is thus ascertained as a difference in relation to the bulk material, an appropriately strong measuring signal being able to be obtained by the series circuit of a high number of thermocouple pairs.

The two thermopile measuring structures thus convert the heating of the particular diaphragms into electrical voltages, so that two measuring signals are output, from which the gas concentration may be ascertained.

Such a construction of a spectroscopic sensor or gas sensor thus requires a suitable space requirement on the sensor chip as well as the space requirement and processing complexity of implementing contact pads and the contacting of the sensor chip, in order to read out the measuring signals.

BRIEF SUMMARY OF THE INVENTION

A measuring structure is implemented according to the present invention between the measuring diaphragm and the reference diaphragm. A direct differential measurement of the temperatures of the two sensitive detector surfaces on the measuring diaphragm and the reference diaphragm is thus made possible according to the present invention.

If the measuring structure is implemented as a thermopile measuring structure having a series circuit of multiple thermocouple pairs, the alternating first and second contacts may thus be implemented on the two diaphragms, i.e., for example, the first contact on the measuring diaphragm and the second contact on the reference diaphragm. A single measuring signal may thus be output according to the present invention, which is formed directly as thermoelectric voltage by the temperature differential between the two sensitive detector surfaces of the measuring diaphragm and the reference diaphragm and is preferably proportional to the temperature differential. This measuring signal may be viewed as a direct measure of the gas concentration and is independent of the luminosity of the IR radiation source in substantial ranges.

Several advantages result according to the present invention. In contrast to typical two-channel implementations, in which the two channels each perform differential measurements with respect to the bulk material, which are separately output, electronically amplified, and then calculated, according to the present invention, interference due to amplifier noise and numeric errors during the calculation may be minimized. Furthermore, the complexity of the implementation of the thermopile structures and the contacting is reduced. A measuring signal may be output directly as a function of the temperature differential and then processed.

The thermopile legs of the thermopile structure each extend from one diaphragm via a gap implemented on the bulk material, for example, to the other diaphragm. They may have a sawtoothed and essentially symmetrical design between the diaphragms, for example. The structuring of the sensor substrate may be implemented for this purpose from the surface in surface micromechanics, or also by bulk micromechanics from both sides.

According to the present invention, only the shared measuring structure may be implemented for the direct ascertainment of the temperature differential according to one example embodiment.

Furthermore, it is also possible according to the present invention to provide at least one further thermal element or one temperature measuring device on at least one diaphragm in addition to the shared measuring structure. In this way, a higher hardware outlay and the processing of two or more signals do again become necessary; however, other evaluations may be performed through this additional outlay.

Therefore, an additional thermal element may only be implemented on one of the diaphragms, for example. In particular, thermopile auxiliary structures may be implemented which have alternating contacts between the particular diaphragm and the bulk material. In an example embodiment having two such thermopile auxiliary structures, the thermopile structure according to the present invention is thus provided for the direct ascertainment of the temperature differential of the diaphragms or the detector surfaces, in addition to the two thermopile auxiliary structures. These thermopile auxiliary structures may have a smaller design than in typical systems, however. A system having three measuring signals results, for example, which, in addition to the use of the differential, also allows the processing of the already typically known measuring signals. This is based on the consideration that a typical evaluation is partially based on a quotient calculation of the measuring signals, but first a measuring signal is obtained as a function of the difference of the temperature of the two diaphragms by the thermopile structure according to the present invention between the two diaphragms, and additional or more precise evaluations are thus made possible due to the varying type and quality of the signals.

In addition to the application as a photometric or a spectroscopic gas sensor, the use as a thermal element is additionally also possible, for example, in an IR camera, since a high degree of integration is possible according to the present invention.

DETAILED DESCRIPTION OF THE INVENTION

Figure 1:
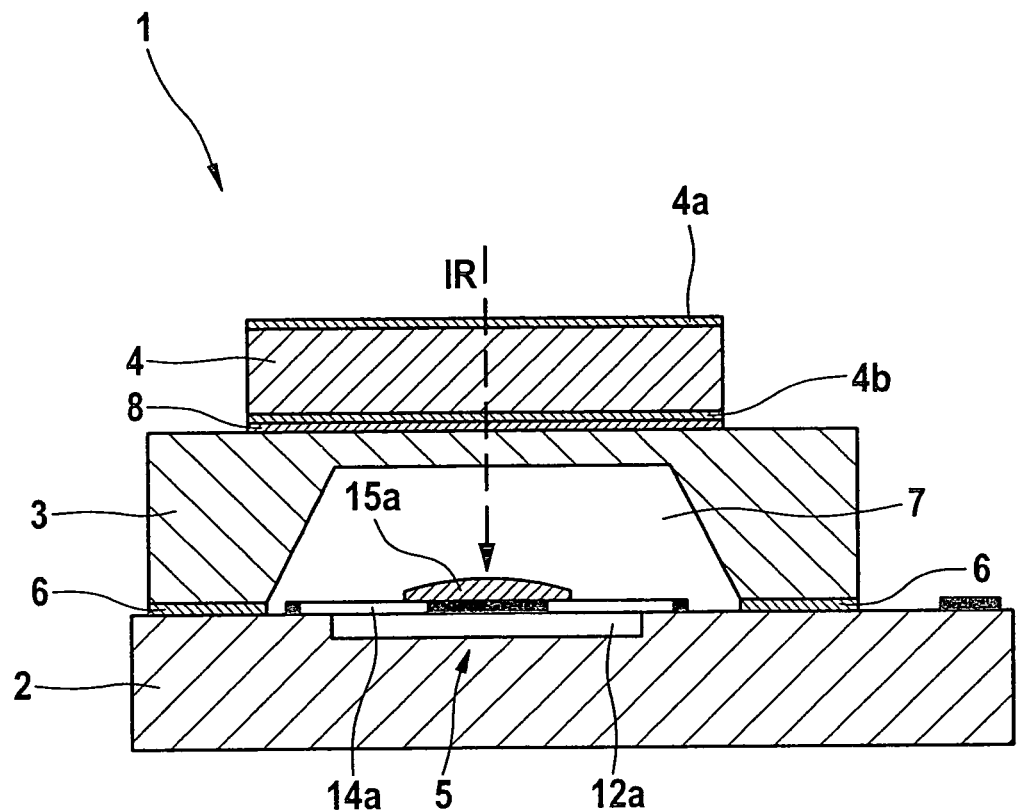
FIG. 1 shows a sensor according to the present invention in vertical section.

According to FIG. 1, a sensor 1 has a sensor substrate 2, a cap substrate 3, and a filter substrate 4 or filter chip, which are implemented as a shared stack or chip stack.

Figure 2:
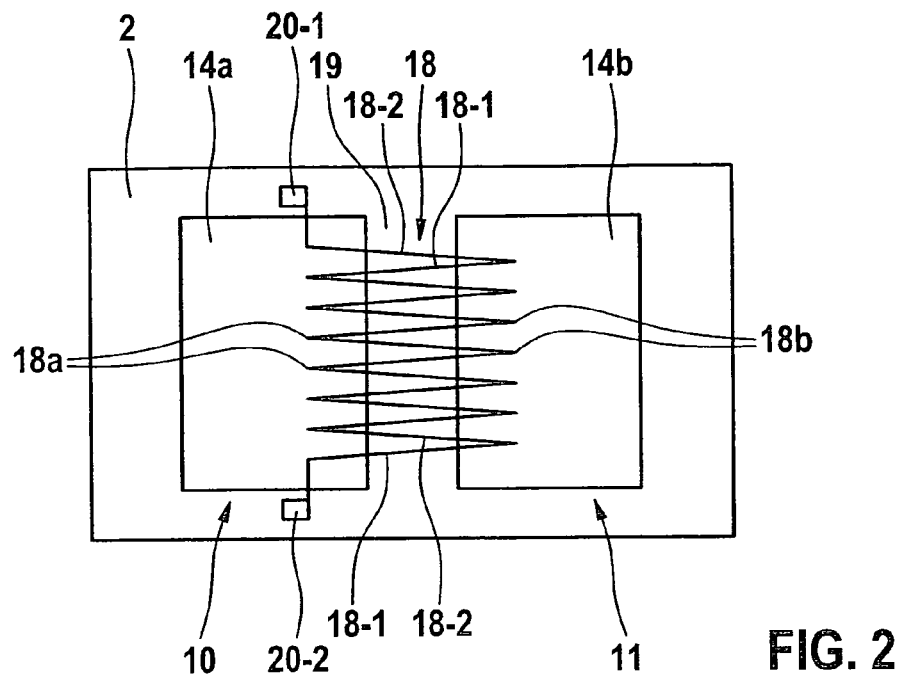
FIG. 2 shows a top view of the sensor substrate having the structured diaphragms from FIG. 1.
Figure 3:
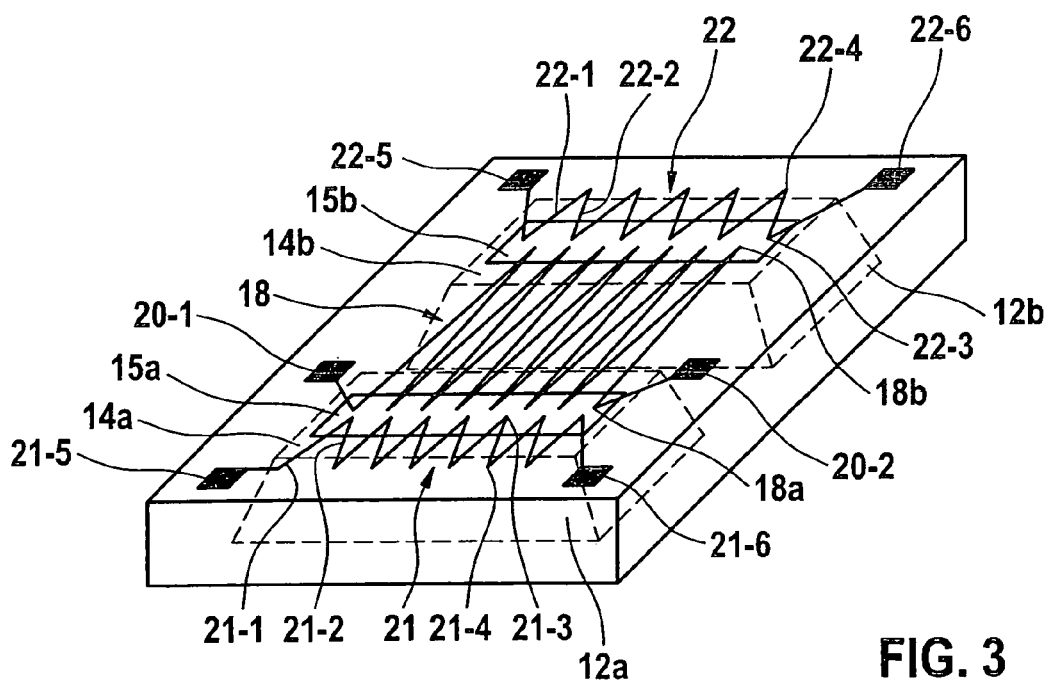
FIG. 3 shows a perspective view of the sensor substrate having the structured diaphragms according to a further example embodiment.

A sensitive detector structure 5, which has a measuring channel 10 and a reference channel 11, which are shown in greater detail in FIGS. 2 and 3, is implemented on the upper side of sensor substrate 2. Cap substrate 3 is fastened on its lower side using a vacuum-tight seal glass connection 6 on the upper side of sensor substrate 2 outside detector structure 5, so that a cavity 7, which is implemented on the lower side of cap substrate 3, receives detector structure 5 in a vacuum. Filter substrate 4 is fastened on the upper side of cap substrate 3 via an IR-transparent adhesive layer 8. Filter substrate 4 is advantageously structured in such a way that it filters incident IR radiation IR selectively by wavelength and transmits IR radiation of a specified wavelength range in each case to measuring channel 10 and reference channel 11. For this purpose, two filter substrates 4 may be applied laterally adjacent to one another on cap substrate 3, which are structured in a way known per se on their upper side and/or lower side using filter layers 4a, 4b. Alternatively to applying filter substrates 4 on cap substrate 3, the wavelength-selective filtering may also be performed via filters, for example, which are attached in a suitable window in a chip housing which receives the sensor.

IR sensitive detector structure 5 has a measuring channel 10 and a reference channel 11 in the specific embodiment shown. For this purpose, for example, multiple measuring channels 10 may also be provided with a shared reference channel 11, in order to detect multiple gas components.

In the case of implementation as a spectroscopic $CO_2$ sensor, cap substrate 3 above measuring channel 10 transmits IR radiation at 4.2 μm, for example, to detect an absorption band of $CO_2$. Correspondingly, cap substrate 3 above reference channel 11 transmits, for example, IR radiation in a reference wavelength range without relevant absorption of IR radiation, for example, at 4.0 μm. In this case, in addition to sensor 1, an IR radiation source and, between the IR radiation source and sensor 1, a measuring section for receiving the gas mixture to be studied are provided.

Measuring channel 10 and reference channel 11 each have a cavity 12a, 12b, which is implemented in sensor substrate 2. A cantilevered measuring diaphragm 14a is implemented above cavity 12a and attached to the bulk material of sensor substrate 2 laterally to cavity 12a; or correspondingly, a reference diaphragm 14b is implemented cantilevered above cavity 12b and attached laterally to cavity 12b. In the case of a superficial-micromechanical implementation according to FIG. 1, cavities 12a, 12b extend from the upper side somewhat into the bulk material of sensor substrate 2. In the case of a bulk-micromechanical implementation according to FIG. 3, cavities 12a, 12b may similarly extend up to the lower side of substrate 2 and may be implemented, for example, by KOH etching.

In the perspective view of FIG. 3, the distance of measuring channel 10 and reference channel 11 in the y direction is shown somewhat enlarged, in order to separate the structures somewhat for the sake of clarity.

Absorption layers 15a, 15b, which absorb the incident IR radiation and heat up correspondingly as sensitive detector surfaces, are implemented in each case on measuring diaphragm 14a and reference diaphragm 14b. Diaphragms 14a, 14b are implemented in a way known per se from electrically insulating material, for example, as a layer or layer system made of ceramic materials, such as $SiO_2$, both diaphragms 14a, 14b being able to be implemented from the point of view of processing technology as parts of a shared layer or a shared layer system, for example.

According to FIG. 2, a thermopile measuring structure 18 is implemented on sensor substrate 2 as a series circuit of thermocouple pairs, each thermocouple pair having two thermopile legs 18-1 and 18-2, which are implemented from conductive materials having different Seebeck coefficients, in particular from different doped semiconductor materials, such as n-Si and p-Si. Alternating thermopile legs 18-1, 18-2 are each contacted with one another in first thermal contacts 18a and second thermal contacts 18b and thus form a zigzag shape extending over both diaphragms 14a, b and optionally a bulk area 19 between diaphragms 14a, b. Therefore, a measuring voltage may be recorded as a voltage signal corresponding to the temperature differential of first contacts 18a and second contacts 18b at contact pads 20-1, 20-2 by corresponding bonding of contact wires.

According to the present invention, first thermal contacts 18a are implemented in or on measuring diaphragm 14a and second thermal contacts 18b are implemented in or on reference diaphragm 14b, advantageously below absorption layers 15a, 15b. Thermopile legs 18-1, 18-2 may run on diaphragms 14a, 14b below absorption layers 15a, 15b or also in or below the diaphragms.

Furthermore, additional thermopile auxiliary structures 21, 22 may be provided according to FIG. 3, which are again implemented as a series circuit of thermopile legs 21-1, 21-2 or 22-1 and 22-2 and whose thermal contacts lie, on the one hand, on particular diaphragm 14a, 14b and, on the other hand, in the bulk material. First thermopile auxiliary structure 21 thus has thermopile legs 21-1, 21-2 made of materials having different Seebeck coefficients, thermal contacts 21-3 lying on measuring diaphragm 14a and second thermal contacts 21-4, which alternate therewith, lying in the bulk material, i.e., outside measuring diaphragm 14. Second thermopile auxiliary structure 22 is implemented symmetrically to first thermopile auxiliary structure 21, having a series circuit of thermopile legs 22-1, 22-2 made of materials having different Seebeck coefficients, whose alternating first thermal contacts 22-3 are implemented on reference diaphragm 14b and second thermal contacts 22-4 are implemented outside reference diaphragm 14b, i.e., on the bulk material of sensor substrate 2. The implementation of FIG. 3 may thus be kept largely symmetrical. Particular contact pads 20-1, 20-2 and 21-5, 21-6, 22-5, and 22-6 lie outside the diaphragms, preferably in a symmetrical arrangement.

According to the implementation of FIG. 2, there is a smaller implementation of thermocouple pairs and only a single measuring signal is output at the contact pads in contrast to a typical system, which essentially has thermopile auxiliary structures 21, 22 according to FIG. 3. According to the present invention, it is additionally possible in FIG. 2 to provide an IR-sensitive photodiode, for example, on one of diaphragms 14a, 14b, for example, and contact it, in order to obtain a further signal in addition to these differential signals.

In FIG. 3, the implementation of additional thermopile measuring structure 18 is provided in contrast to a typical implementation, thermopile structures 18, 21, and 22 being able to be implemented in shared processing steps and from identical materials. According to FIG. 3, more precise measuring is possible, because, on the one hand, the differential measurement according to FIG. 2, and, on the other hand, the individual measurements in measuring channel 10 and reference channel 11, may also be performed.

Fundamentally, according to the present invention, the measuring diaphragm and the reference diaphragm may also be implemented as subareas of a shared diaphragm, i.e., above a shared cavity, the sensitive detector surfaces having the absorption layers being separated accordingly.

Furthermore, the sensor according to the present invention has a control unit and evaluation electronics for receiving and evaluating the at least one measuring signal, and a sensor housing or chip housing, which receives chips or substrates 2, 3, 4, the IR radiation source and sensor 1 being able to be accommodated on a shared circuit carrier.

What is claimed is:

1. A microstructured sensor for detecting IR radiation, comprising:
   one measuring channel having a measuring diaphragm, wherein a first sensitive detector surface is implemented on the measuring diaphragm for the absorption of a first IR radiation;
   one reference channel having a reference diaphragm, wherein a second sensitive detector surface is implemented on the reference diaphragm for the absorption of a second IR radiation;
   a measuring structure implemented between the measuring diaphragm and the reference diaphragm for measuring a temperature differential between the measuring diaphragm and the reference diaphragm;
   a sensor substrate, wherein the measuring structure is implemented on the upper side of the sensor substrate, and wherein the measuring diaphragm is implemented above a first cavity of the sensor substrate, and wherein the reference diaphragm is implemented above a second cavity of the sensor substrate;
   a cap substrate having at least one cavity, wherein the measuring diaphragm and the reference diaphragm are positioned one of below or in the at least one cavity of the cap substrate; and
   contact terminals for the measuring structure, wherein the contact terminals are implemented on the sensor substrate outside the measuring diaphragm and the reference diaphragm;
   wherein the measuring structure is implemented as a thermopile measuring structure having a series circuit made of multiple thermocouple pairs, each thermocouple pair having a first thermopile leg and a second thermopile leg, and wherein the first and second thermopile legs include materials having different Seebeck coefficients, and wherein the first and second thermopile legs are contacted with one another in alternating first contacts and second contacts, the first contacts being implemented one of in or on the measuring diaphragm, and the second contacts being implemented one of in or on the reference diaphragm;
   wherein the first and second thermopile legs of the thermopile measuring structure each extend from the first sensitive detector surface on the measuring diaphragm to the second sensitive detector surface on the reference diaphragm.

2. The sensor as recited in claim 1, wherein the first and second thermopile legs of the thermopile measuring structure each extend from the measuring diaphragm to the reference diaphragm via a bulk area located between the measuring diaphragm and the reference diaphragm.

3. The sensor as recited in claim 1, wherein the first thermopile legs and second thermopile legs form a zigzagging course.

4. The sensor as recited in claim 1, wherein absorber layers configured to absorb incident IR radiation are implemented as the first and second sensitive detector surfaces.

5. The sensor as recited in claim 1, wherein the measuring channel and the reference channel are implemented symmetrically, the measuring diaphragm and the reference diaphragm being identically dimensioned, and wherein the measuring structure is implemented substantially symmetrically between the measuring diaphragm and the reference diaphragm.

6. A microstructured sensor for detecting IR radiation, comprising:
   one measuring channel having a measuring diaphragm, wherein a first sensitive detector surface is implemented on the measuring diaphragm for the absorption of a first IR radiation;
   one reference channel having a reference diaphragm, wherein a second sensitive detector surface is implemented on the reference diaphragm for the absorption of a second IR radiation;
   a measuring structure implemented between the measuring diaphragm and the reference diaphragm for measuring a temperature differential between the measuring diaphragm and the reference diaphragm; and
   at least one further temperature sensor configured to output at least one second measuring signal, wherein the at least one further temperature sensor is provided on at least one of the measuring diaphragm and the reference diaphragm;
   wherein the measuring structure is implemented as a thermopile measuring structure having a series circuit made of multiple thermocouple pairs, each thermocouple pair having a first thermopile leg and a second thermopile leg, and wherein the first and second thermopile legs include materials having different Seebeck coefficients, and wherein the first and second thermopile legs are contacted with one another in alternating first contacts and second contacts, the first contacts being implemented one of in or on the measuring diaphragm, and the second contacts being implemented one of in or on the reference diaphragm;
   wherein the first and second thermopile legs of the thermopile measuring structure each extend from the first sensitive detector surface on the measuring diaphragm to the second sensitive detector surface on the reference diaphragm.

7. A microstructured sensor for detecting IR radiation, comprising:

one measuring channel having a measuring diaphragm, wherein a first sensitive detector surface is implemented on the measuring diaphragm for the absorption of a first IR radiation;

one reference channel having a reference diaphragm, wherein a second sensitive detector surface is implemented on the reference diaphragm for the absorption of a second IR radiation;

a measuring structure implemented between the measuring diaphragm and the reference diaphragm for measuring a temperature differential between the measuring diaphragm and the reference diaphragm;

a first thermopile auxiliary structure implemented between the measuring diaphragm and a bulk area outside the measuring diaphragm and the reference diaphragm; and a second thermopile auxiliary structure implemented between the reference diaphragm and the bulk area outside the measuring diaphragm and the reference diaphragm;

wherein the first and second thermopile auxiliary structures have contact terminals for outputting a second measuring signal and a third measuring signal;

wherein the measuring structure is implemented as a thermopile measuring structure having a series circuit made of multiple thermocouple pairs, each thermocouple pair having a first thermopile leg and a second thermopile leg, and wherein the first and second thermopile legs include materials having different Seebeck coefficients, and wherein the first and second thermopile legs are contacted with one another in alternating first contacts and second contacts, the first contacts being implemented one of in or on the measuring diaphragm, and the second contacts being implemented one of in or on the reference diaphragm;

wherein the first and second thermopile legs of the thermopile measuring structure each extend from the first sensitive detector surface on the measuring diaphragm to the second sensitive detector surface on the reference diaphragm.

8. A microstructured sensor for detecting IR radiation, comprising:

one measuring channel having a measuring diaphragm, wherein a first sensitive detector surface is implemented on the measuring diaphragm for the absorption of a first IR radiation;

one reference channel having a reference diaphragm, wherein a second sensitive detector surface is implemented on the reference diaphragm for the absorption of a second IR radiation; and a measuring structure implemented between the measuring diaphragm and the reference diaphragm for measuring a temperature differential between the measuring diaphragm and the reference diaphragm;

wherein the measuring structure is implemented as a thermopile measuring structure having a series circuit made of multiple thermocouple pairs, each thermocouple pair having a first thermopile leg and a second thermopile leg, and wherein the first and second thermopile legs include materials having different Seebeck coefficients, and wherein the first and second thermopile legs are contacted with one another in alternating first contacts and second contacts, the first contacts being implemented one of in or on the measuring diaphragm, and the second contacts being implemented one of in or on the reference diaphragm;

wherein the first and second thermopile legs of the thermopile measuring structure each extend from the first sensitive detector surface on the measuring diaphragm to the second sensitive detector surface on the reference diaphragm;

wherein the sensor is a spectroscopic gas sensor configured to determine at least one gas concentration, and wherein the measuring channel and the reference channel each have a spectroscopic IR filter for the selective transmission of a first IR radiation in a measuring wavelength range and a second IR radiation in a reference wavelength range.

9. The sensor as recited in claim 1, wherein the sensor is configured as an IR thermometer.

* * * * *